(12) United States Patent
García De Castro Andrews et al.

(10) Patent No.: US 9,271,927 B2
(45) Date of Patent: Mar. 1, 2016

(54) FORMULATION OF DRUGS AND VACCINES IN THE FORM OF PERCUTANEOUS INJECTABLE NEEDLES

(75) Inventors: Arcadio García De Castro Andrews, Madrid (ES); Raúl García Carrodeaguas, Madrid (ES); Niuris Acosta Contreras, Madrid (ES)

(73) Assignee: AZUREBIO, S.L., Madrid (ES)

( * ) Notice: Subject to any disclaimer, the term of this patent is extended or adjusted under 35 U.S.C. 154(b) by 6 days.

(21) Appl. No.: 13/500,279

(22) PCT Filed: Oct. 8, 2010

(86) PCT No.: PCT/EP2010/065106
§ 371 (c)(1),
(2), (4) Date: May 15, 2012

(87) PCT Pub. No.: WO2011/042542
PCT Pub. Date: Apr. 14, 2011

(65) Prior Publication Data
US 2012/0219589 A1 Aug. 30, 2012

(30) Foreign Application Priority Data
Oct. 8, 2009 (ES) .................................. 200930820

(51) Int. Cl.
*A61K 39/29* (2006.01)
*A61K 38/16* (2006.01)
(Continued)

(52) U.S. Cl.
CPC ............... *A61K 9/0021* (2013.01); *A61K 39/12* (2013.01); *A61K 39/292* (2013.01);
(Continued)

(58) Field of Classification Search
CPC .............. A61K 9/0021; A61K 39/292; A61K 41/0042; A61K 2039/54; A61K 2039/55555; A61K 2039/55561; A61K 9/1623; A61M 37/0069; C12N 2730/10134; C08F 220/06; C08F 220/56; C08F 220/58; C08F 222/10; C08F 222/1006; C08F 222/32
See application file for complete search history.

(56) References Cited

U.S. PATENT DOCUMENTS

| 4,326,524 | A  | * | 4/1982 | Drake et al. ................... 424/422 |
| 7,056,957 | B2 | * | 6/2006 | Omidian et al. ................ 521/99 |
| 2003/0170306 | A1 | * | 9/2003 | Raether et al. ................. 424/484 |

FOREIGN PATENT DOCUMENTS

| EP | 0139286 A2 | 5/1985 |
| EP | 139286 A2 * | 5/1985 ............... A61K 9/00 |

(Continued)

OTHER PUBLICATIONS

Lin SY, Cheng LF, Lui WY, Wu LH, Kao SJ, Han SH. "Controlled release of adriamycin HCl from polymeric needle devices" Biomater Artif Cells Artif Organs. 1988;16(4):801-14.*

(Continued)

*Primary Examiner* — Ileana Popa
*Assistant Examiner* — Nicole Babson
(74) *Attorney, Agent, or Firm* — Blank Rome LLP

(57) ABSTRACT

The invention relates to percutaneous administration of drugs and vaccines in form of solid penetrating needles, "injectable needles", comprising a polymeric matrix resulting from the polymerization of a polymerizable paste or mixture. The injectable needles are hard enough to penetrate the skin and can be administered percutaneously by simple pusher or injector delivery devices. The manufacturing procedure of the injectable needles allows for the incorporation of the drug as preformulated stable microparticles and incorporation of modifying agents to modulate stiffness, solubility and drug release. Drugs formulated in these injectable needles offer a safe, simple and effective alternative to conventional percutaneous drug delivery systems based on hypodermic needles and syringes that require refrigerated storage and reconstitution prior to administration.

6 Claims, 4 Drawing Sheets

(51) Int. Cl.
- *A61K 38/38* (2006.01)
- *A61K 38/47* (2006.01)
- *A61K 9/00* (2006.01)
- *A61K 41/00* (2006.01)
- *A61M 37/00* (2006.01)
- *A61K 39/12* (2006.01)
- *A61K 9/16* (2006.01)
- *A61K 39/00* (2006.01)
- *C08F 220/06* (2006.01)
- *C08F 220/56* (2006.01)
- *C08F 220/58* (2006.01)
- *C08F 222/10* (2006.01)
- *C08F 222/32* (2006.01)

(52) U.S. Cl.
CPC ....... *A61K 41/0042* (2013.01); *A61M 37/0069* (2013.01); *A61K 9/1623* (2013.01); *A61K 2039/54* (2013.01); *A61K 2039/55555* (2013.01); *A61K 2039/55561* (2013.01); *A61K 2039/57* (2013.01); *C08F 220/06* (2013.01); *C08F 220/56* (2013.01); *C08F 220/58* (2013.01); *C08F 222/10* (2013.01); *C08F 222/1006* (2013.01); *C08F 222/32* (2013.01); *C12N 2730/10134* (2013.01)

(56) References Cited

FOREIGN PATENT DOCUMENTS

| WO | WO-8706129 A1 | 10/1987 |
| WO | WO-0057852 A2 | 10/2000 |
| WO | WO 2008102136 A2 * | 8/2008 |
| WO | WO-2009047276 A1 | 4/2009 |
| WO | WO-2009103513 A1 | 8/2009 |

OTHER PUBLICATIONS

Lin SY, Cheng LF, Lui WY, Chen CF, Han SH "Tumoricidal effect of controlled-release polymeric needle devices containing adriamycin HCI in tumor-bearing mice" Biomater Artif Cells Artif Organs. 1989;17(2):189-203.*

Khin Yin Win, Si-Shen Feng, "Effects of particle size and surface coating on cellular uptake of polymeric nanoparticles for oral delivery of anticancer drugs" Biomaterials, vol. 26, Issue 15, May 2005, pp. 2713-2722.*

A Hatefi, B Amsden, Biodegradable injectable in situ forming drug delivery systems, Journal of Controlled Release, vol. 80, Issues 1-3, Apr. 23, 2002, pp. 9-28.*

International Search Report issued in PCT/EP2010/065106 on Mar. 25, 2011.

* cited by examiner

FORMULATION OF DRUGS AND VACCINES IN THE FORM OF PERCUTANEOUS INJECTABLE NEEDLES

This application is the U.S. national phase of International Application No. PCT/EP2010/065106, filed Oct. 8, 2010, which claims the benefit of Spanish Patent Application No. P200930820, filed Oct. 8, 2009.

FIELD OF THE INVENTION

The invention relates to formulations for percutaneous administration of drugs and vaccines in form of solid penetrating needles, "injectable needles", which are inserted through the epidermis by simple pusher or injector devices. Once injected into the tissues the injectable needles release the contained drug and are biodegradable or bioresorbable.

In particular, the injectable needles of the present invention are monoliths manufactured by means of polymerization processes which permit the incorporation of drugs and vaccines and result in injectable needles hard enough to penetrate the skin upon the action of a momentary force applied by a pusher or injector device.

These injectable needles offer a safe, simple and effective alternative to conventional percutaneous drug delivery systems based on hypodermic needles and syringes, and drugs that require refrigerated storage and reconstitution prior to administration.

BACKGROUND OF THE INVENTION

Many drugs are administered percutaneously, either intradermal, subcutaneous or intramuscular, by injection by qualified medical personnel. This involves a first step in reconstituting the drug with sterile water, a second step of loading of the syringe with an appropriate volume of the reconstituted drug, and a third step of administration to the patient by means of a sterile hypodermic needle.

This injection process can be problematic, especially in locations and conditions where technical and material resources are limited. In particular, many biologically active molecules and preparations require refrigeration during transport and storage, and failure of cold chain results in the loss of large amounts of drugs. Moreover, the need for reconstitution with sterile water can also represent a problem in cases of microbial contamination or use of incorrect volumes. The potential reuse of the syringe and hypodermic needles following administration of the drug also represents a serious risk of transmitting infectious agents such as hepatitis or human immunodeficiency virus (HIV). These problems are particularly acute in the administration of vaccines in the underdeveloped and developing world where the World Health Organization has recognized the need for alternative drug delivery methods (Jodar L et al. 1998 Revolutionising Immunisations. Genetic Engineering News 18-4; y Clements C J et al. 2004 Technologies that make administration of vaccines safer. Vaccine 22:2054-2058).

In general the alternative methods proposed to date for the percutaneos administration of drugs and vaccines solve some of the drawbacks of conventional hypodermic needles and syringes but do not appear to solve all the inconvenient in one single delivery format-device. Examples of this are device packages with colorimetric indicators that warn of the failure of the cold chain of storage. Other examples of these partial solutions are devices based on conventional needles and syringes that incorporate self-destruct mechanisms that prevent possible reuse. In general these devices are more expensive than conventional syringes and needles and do not avoid the need for refrigeration, reconstitution and requirement for skilled personnel for administration. Another approach, described for example in U.S. Pat. No. 4,891,319 is the stabilization of drugs by adding excipients, as is the case of trehalose, which avoid the need for cold chain but still require reconstitution prior to injection. To avoid this need for reconstitution, patent WO02/032402 proposes the suspension of drugs in microparticles stabilized in non-aqueous liquids that facilitate their injection. Still, the administration of these suspensions requires conventional devices incorporating hypodermic needles or complex liquid-jet devices. Other alternatives, such as proposed in WO97/48485, include the administration of drug-containing particles using "ballistic" devices. A problem with these systems is the need for delivery devices that provide considerable injection force by means of powerful springs, explosions, or high-speed liquid jets. Therefore these approaches cannot provide a means of administering drugs at the required depth by means of simple easy to use low-cost disposable devices.

An alternative method in the administration of vaccines that theoretically avoids the need for refrigeration, reconstitution, needles and complex devices, is the formulation of drugs in ready to injected solid formats. This approach has been explored in the design of high speed projectiles administered by devices that resemble firearms, and, alternatively, by slow speed penetrating "injectable needles" administered by devices in direct contact with the skin.

Examples of drug delivery by means of projectiles are incorporated in patent WO96/140351, which includes large projectiles (7×5 mm) formed by a solid plastic head and a hollow cylindrical body containing the drug. Due to their large size, as an alternative form of administration, it is suggested that the doctor or veterinarian performs an incision and manually inserts the projectile under the skin. U.S. Pat. No. 3,948,263 and U.S. Pat. No. 4,326,524 also refer to ballistic devices in which the drug is shot by 0.25-caliber rifles. In particular, U.S. Pat. No. 4,326,524 mentions drug formulations in the form of solid particles and cohesive agents that provide the projectile with enough strength to withstand firing and subsequent impact. The projectiles described have a diameter of between 4.5 and 7.6 mm and a geometry that facilitates flight. U.S. Pat. No. 3,901,158 and CA1019638 also incorporate glass or plastic ballistic devices that break on impact releasing the encapsulated active drug and its application is mainly for veterinary use.

Different to the concept of "projectiles" is the concept of "injectable needles" with dimensions and hardness that permit administration by simple pusher or injector devices in direct contact with the skin. By definition these needles must be small, have the strength and rigidity necessary for injection, and allow for the incorporation of drugs and vaccines. As an example, patent EP0139286 describes needles or bars administrated by injection and made from biocompatible organic polymers such as collagen, gelatin, albumin or chitin. The patent describes administration of these needles through hollow needles, presumably due to a lack of stiffness or hardness. The document emphasizes avoiding the immune response caused by the needle and does not suggest their potential application in the field of vaccines.

One obvious problem in the manufacture of injectable needles from aqueous or organic polymers in solution is the reduction in volume that results from the evaporation of water or solvent in the drying process. This represents a real problem in the production of needles with the desired size. Patent WO94/22423 identifies this problem and the need for needle with appropriate strength for injection, and proposes as alternative production method the extrusion from the mixture of the active ingredient with an excipients and polymers. Preferred excipients and polymers described are those soluble in aqueous media such as gelatine, collagen, cellulose, agarose or albumin. The patent does not develop in particular the applicability of needle injections into the field of vaccines. Furthermore, U.S. Pat. No. 5,081,156 and U.S. Pat. No. 4,855,134 describe interferon or indomethacin formulations incorporating collagen, gelatine or albumin as excipients and propose formulations in the form of needles or bars from the drying of a mixture or powder compression. The resulting needles seem to lack the rigidity necessary for direct injection and surgical insertion and use of catheters are described as a means for insertion. U.S. Pat. No. 5,542,920 describes simple devices for incorporation of injection needles with a pointed end and rigid enough to penetrate the skin. The needles have a preferred diameter between 0.2 and 0.8 mm and about 10 to 30 mm long. The excipients mentioned in the manufacture of the needles are preformed polymers like jelly polyvinylpyrrolidone or poly (lactic-co-glycolic acid). Neither in these documents there is a special mention of its application in the field of vaccines, nor methods for these needles to be effective in vaccination, nor the incorporation of modifying agents to increase hardness. Also, the U.S. Pat. No. 6,102,896 is also focused on the design of an injector for administering injectable soluble needles containing drugs and once again recognizes the difficulty in formulating these needles with the necessary rigidity without compromising the activity of the incorporated drug. As an example, the document recognizes the inconveniences of using phosphate or metal carboxylate glasses because of the high temperatures required for their fusion, and propose the use of sugar based powders that can be suspended in a solvent for their incorporation into narrow tubes for the manufacture of the needles.

Heterogeneous needles containing a drug either in solution or homogeneously dispersed have also been proposed as an alternative for making injectable needles with the strength required to penetrate the skin. A realization of these heterogeneous injectable needles is described in the patent WO/03023773 in which needles are composed of a soluble solid tip, followed by the drug in the form of a liquid, solid or paste. The proposed materials for the manufacture of the soluble tip include glass of sugars. The document does not provide technical solutions for the manufacture of these heterogeneous needles, but acknowledges that formulations containing residual water result in degradation of the contained actives. The devices described for administration of the proposed formulations incorporate an added complexity that can be expected to result in high-cost devices. Another realization of heterogeneous miniprojectiles is described in patent WO96/09070 and Van de Wijdeven 2002 "Development and assessment of mini projectiles as drug carriers" in the J. of Controlled Release 85:145-162 where extruded starch hollow fibres with a sharp end are filled with different drugs and vaccines and used as mini projectiles. These heterogeneous needles are large, typically 16 mm in length and 3 mm in diameter, and usually require compressed air nozzles or minor surgery for their delivery or implantation.

Injectable needles described so far have serious drawbacks. Mainly, the difficulty in manufacturing uniform needles that preserve the integrity of drug, and the difficulty in producing needles with the size shape and hardness required to pass through skin. It is therefore desirable to find a biocompatible formulation and method of manufacture that permits the efficient incorporation of drugs and vaccines in injection needles without compromising biological activity and that result in injectable needles which are sufficiently robust to be injected subcutaneously by simple pusher devices or nozzles in direct contact with skin.

The present invention relates to solid monolithic injectable needles for percutaneous, administration, including intradermal, subcutaneous or intramuscular locations, of drugs and vaccines which are partially or wholly formed by a polymer matrix resulting from a polymerization process in which drugs are incorporated. The manufacture of injectable needles by polymerization reactions described in the present invention enables fast and effective incorporation of the drugs, vaccines and other biological actives to the polymer and result in injectable needles with the optimum size, hardness and rigidity necessary to penetrate the skin. The procedures described in the present invention allow the manufacture of injectable needles that contain drugs and vaccines and may also contain modifying agents able to provide the necessary hardness to the resulting material to pass through the skin tissue under the action of a manual effort, modulate the profile of degradation of the matrix, the release profile, and/or enhance the immune response or stability of the contained drug or vaccine.

SUMMARY OF THE INVENTION

The present invention describes "injectable needles" containing drugs, vaccines and other biologically active substances, which incorporate biodegradable or bioresorbable polymeric materials with enough hardness and stiffness for percutaneous, including intradermal, subcutaneous or intramuscular administration, by simple injector or pusher dispenser devices. The injectable needles described, applied to the administration of drugs and vaccines, avoid the need for qualified staff, cold chain, reconstitution with sterile water, and potential reuse of needles and syringes. This is of application in the fields of animal and human health and of particular interest in third world countries or in case of humanitarian campaigns during catastrophes or situations requiring self-administration of drugs and vaccines.

Injectable needles of the present invention result from polymerization processes that incorporate the active drug or vaccine. During manufacture, polymerizable substances, or the material resulting from their polymerization, are shaped in the form of a solid injectable needle. These polymerization processes involve the transformation of a liquid or semisolid phase, typically a paste or mixture, containing monomers and other components of a polymerization reaction, optional modifying agents, and the drug or vaccine into a solid monolithic body in the shape of an injectable needle. The injectable needle is made to have the shape, hardness and stiffness required to pass through the skin tissue, reaching dermal, subcutaneous, or muscle tissue, and releasing the drug or vaccine in situ. The polymerization processes include polymerization reactions by anionic addition or radical addition originated by polymerizable mono-functional or multi-functional monomers. Polymerization processes referred to in the present invention permit the direct incorporation of drugs and vaccines, or their incorporation in the form of preformulated nano- or micro-particles made to preserve the integrity and therapeutic action drug or vaccine they contain during the manufacture of the injectable needle and subsequent storage. The polymerization processes can be made to incorporate modifying agents to increase hardness and rigidity of the resulting injectable needles, modify their rate of degradation or drug or vaccine release profile.

DESCRIPTION OF THE INVENTION

One aspect of the present invention relates to an injectable needle comprising a polymeric matrix made to incorporate a drug during a polymerization process.

In another embodiment, the invention relates to the injectable needle defined above wherein at least 20% in mass of the injectable needle is formed by a polymeric matrix resulting from a polymerization process.

In another embodiment, the invention relates to the injectable needle defined above wherein the polymeric matrix is at least partially biodegradable or resorbable.

In another embodiment, the invention relates to the injectable needle defined above which polymeric matrix has stiffness over 10 MPa.

In another embodiment, the invention relates to the injectable needle defined above wherein the polymeric matrix consists of an addition polymer formed by one or more addition monomers.

In another embodiment, the invention relates to the injectable needle defined above wherein the addition polymer is an anionic addition polymer.

In another embodiment, the invention relates to the injectable needle defined above wherein the anionic addition polymer is a polycyanoacrylate.

In another embodiment, the invention relates to the injectable needle defined above wherein the polycyanoacrylate is selected from one or more alkyl polycyanoacrylates.

In another embodiment, the invention relates to the injectable needle defined above wherein the alkyl group is a methyl, ethyl, butyl, octyl or any of their combinations thereof.

In another embodiment, the invention relates to the injectable needle defined above in which the addition polymer is a radical addition polymer.

In another embodiment, the invention relates to the injectable needle defined above wherein the radical addition polymer is selected from: polyacrylate, polymethacrylate, polyvinyl or any of their combinations thereof.

In another embodiment, the invention relates to the injectable needle defined above wherein the polyacrylate is selected from: polyacrylic acid, polyacrilamide, poly-N-isopropilacrylamide, alkaline polyacrylate, alkaline-terreous polyacrylate, ammonium polyacrylate, or any of their combinations thereof.

In another embodiment, the invention relates to the injectable needle defined above wherein the polymethacrylate is selected from the list that comprises: polymethacrylic acid, polymetacrylic acid, alkaline polymetacrylate, alkaline-terreous polymetacrylate, ammonium polymetacrylate, 2-hydroxypropil polymetacrylate, (2-dimetilamino)ethyl polymetacrylate, 1-glycerol polymetacrylate, polymetacrylamide, o any of their combinations.

In another embodiment, the invention relates to the injectable needle defined above wherein the polyvinyl is poly-N-vinyl pyrrolidone.

In another embodiment, the invention relates to the injectable needle defined above wherein the polymeric matrix is an addition polymer resulting from polymerization of monofunctional monomers that result in linear polymers.

In another embodiment, the invention relates to the injectable needle defined above wherein the polymer originated by the polymerization of the monofunctional monomers is a polycyanoacrylate, polyacrylate, polymethacrylate, polyvinyl or any of their combinations thereof.

In another embodiment, the invention relates to the injectable needle defined above in which the polymeric matrix contains an addition polymer originated by polymerization of multifunctional monomers.

In another embodiment, the invention relates to the injectable needle defined above wherein the polymer resulting from the polymerization of multifunctional monomers is a polydiacrylate, polytriacrylate, polydimethacrylate, polytrimethacrylate or any of their combinations thereof.

In another embodiment, the invention relates to the injectable needle defined above which further comprises monomers or cross-linkers that contain hydrolysable or cleavable functional groups.

In another embodiment, the invention relates to the injectable needle defined above were the cross-linkers are, di- or triacrylates, or di- or trimethacrilates of polyethylene glycols, pluronics, and functionalised poly(hydroxyl alkanoates) and/or poly(lactide-co-glycolide)s.

In another embodiment, the invention relates to the injectable needle defined above that contains condensation polymers as polymeric modifying agents.

In another embodiment, the invention relates to the injectable needle defined above wherein the condensation polymers are selected from the list: polylactic acid, polyglycolic acid, copolymers of lactic and glycolic acid, polycaprolactone, polyethylenglycol, polyhydroxybutiric acid, valeric acid and any of their combinations thereof.

In another embodiment, the invention relates to the injectable needle defined above that contains polymers of natural origin as polymeric modifying agents.

In another embodiment, the invention relates to the injectable needle defined above in which the natural polymers are selected from the list: cellulose, chitosan, starch, collagen, fibronectin, hyaluronic acid, guar, agar, xanthan, agarose, alginic acid, alginates and any of their derivatives and combinations thereof.

In another embodiment, the invention relates to the injectable needle defined above that contain soluble particulate modifying agents In another embodiment, the invention relates to the injectable needle defined above that contain surfactant modifying agents In another embodiment, the invention relates to the injectable needle defined above that contains reinforcing modifying agents that contributes to increased hardness or rigidity.

In another embodiment, the invention relates to the injectable needle defined above in which reinforcing modifying agents are selected from metal oxides, bioglasses, calcium salts, carbonates, phosphates, silicates, aluminates, circonates or other metals and any of their combinations thereof.

In another embodiment, the invention relates to the injectable needle defined above that contains modifying agents with adjuvant activity.

In another embodiment, the invention relates to the injectable needle defined above in which the modifying agents with adjuvant activity are selected from calcium phosphates, aluminium phosphates, aluminium hydroxide, calcium phosphate, saponins, proteasomes, immunostimulating complexes (ISCOM), and mycolic acid and mycolates, pyridina, vitamin A, vitamin E, halides, dimethyldioctadecylammonium (DDA), muramyl dipeptide and tripeptide, monophosphoryl lipid A, trehalose dimycolate, CpG oligodeoxynucleotide motifs, liposomes, cytokines, glucans, dextrans, lentinan, glucomannan, galactomannans, acemanane, interferon, interleukins, virosomes, bacterial toxins, levamisole and any of their combinations thereof.

In another embodiment, the invention relates to the injectable needle defined above in a drug is in solid solution in the polymeric matrix.

In another embodiment, the invention relates to the injectable needle defined above in a drug is in the form of particles or granules in the polymeric matrix.

In another embodiment, the invention relates to the injectable needle defined above wherein the drug is in preformulated particles or granules.

In another embodiment, the invention relates to the injectable needle defined above wherein the preformulated particles or granules contain stabilizing agents, surfactants and/or adjuvants.

In another embodiment, the invention relates to the injectable needle defined above in which the drug is contained in the form of a solid monolith.

In another embodiment, the invention relates to the injectable needle defined above wherein the monolith contains stabilizing agents, surfactants and/or adjuvants.

In another embodiment, the invention relates to the injectable needle defined above wherein:
- at least 20% in mass of the injectable needle is formed by a polymeric matrix resulting from a polymerization process; and
- which polymeric matrix has stiffness over 10 MPa.

In another embodiment, the invention relates to the injectable needle defined above wherein:
- at least 20% in mass of the injectable needle is formed by a polymeric matrix resulting from a polymerization process;
- which polymeric matrix has stiffness over 10 MPa; and
- the polymeric matrix consists of an addition polymer formed by one or more addition monomers.

In another embodiment, the invention relates to the injectable needle defined above wherein:
- at least 20% in mass of the injectable needle is formed by a polymeric matrix resulting from a polymerization process;
- which polymeric matrix has stiffness over 10 MPa;
- the polymeric matrix consists of an addition polymer formed by one or more addition monomers; and
- that contains polymers of natural origin as polymeric modifying agents.

In another embodiment, the invention relates to the injectable needle defined above wherein:
- at least 20% in mass of the injectable needle is formed by a polymeric matrix resulting from a polymerization process;
- which polymeric matrix has stiffness over 10 MPa;
- the polymeric matrix consists of an addition polymer formed by one or more addition monomers;
- that contains polymers of natural origin as polymeric modifying agents; and
- that contains modifying agents with adjuvant activity.

In another embodiment, the invention relates to the injectable needle defined above wherein:
- at least 20% in mass of the injectable needle is formed by a polymeric matrix resulting from a polymerization process;
- which polymeric matrix has stiffness over 10 MPa; and
- in a drug is in solid solution in the polymeric matrix.

In another embodiment, the invention relates to the injectable needle defined above wherein:
- at least 20% in mass of the injectable needle is formed by a polymeric matrix resulting from a polymerization process;
- which polymeric matrix has stiffness over 10 MPa;
- the polymeric matrix consists of an addition polymer formed by one or more addition monomers;
- that contains polymers of natural origin as polymeric modifying agents;
- that contains modifying agents with adjuvant activity; and
- in a drug is in solid solution in the polymeric matrix.

In another embodiment, the invention relates to the injectable needle defined above wherein:
- at least 20% in mass of the injectable needle is formed by a polymeric matrix resulting from a polymerization process;
- which polymeric matrix has stiffness over 10 MPa;
- in a drug is in solid solution in the polymeric matrix; and
- in which the drug is contained in the form of a solid monolith.

In another embodiment, the invention relates to the injectable needle defined above wherein:
- at least 20% in mass of the injectable needle is formed by a polymeric matrix resulting from a polymerization process;
- which polymeric matrix has stiffness over 10 MPa;
- the polymeric matrix consists of an addition polymer formed by one or more addition monomers;
- that contains polymers of natural origin as polymeric modifying agents;
- that contains modifying agents with adjuvant activity;
- in a drug is in solid solution in the polymeric matrix; and
- in which the drug is contained in the form of a solid monolith.

In another embodiment, the invention relates to the injectable needle defined above wherein:
- at least 20% in mass of the injectable needle is formed by a polymeric matrix resulting from a polymerization process;
- which polymeric matrix has stiffness over 10 MPa;
- in a drug is in solid solution in the polymeric matrix;
- in which the drug is contained in the form of a solid monolith; and
- wherein the monolith contains stabilizing agents, surfactants and/or adjuvants.

In another embodiment, the invention relates to the injectable needle defined above wherein:
- at least 20% in mass of the injectable needle is formed by a polymeric matrix resulting from a polymerization process;
- which polymeric matrix has stiffness over 10 MPa;
- the polymeric matrix consists of an addition polymer formed by one or more addition monomers;
- that contains polymers of natural origin as polymeric modifying agents;
- that contains modifying agents with adjuvant activity;
- in a drug is in solid solution in the polymeric matrix;
- in which the drug is contained in the form of a solid monolith; and
- wherein the monolith contains stabilizing agents, surfactants and/or adjuvants.

In another embodiment, the invention relates to a injectable needle as defined above selected from the list described in Examples 1 to 12.

Throughout the present specification, by the term "treatment" refers to procedures to diagnose, preventing, eliminating, reducing or ameliorating the cause or the effects of a disease. For purposes of this invention treatment includes, but is not limited to, diagnosis, prevention, alleviation, amelioration or elimination of one or more symptoms of the disease; diminishment of the extent of the disease, stabilized (i.e. not worsening) state of the disease, delay or slowing of disease progression; amelioration or palliation of the disease state; and remission of the disease (whether partial or total).

The present invention relates to an "injectable needle" partially or wholly formed by a polymer matrix resulting from a polymerization reaction made to incorporate a drug.

That is, that the process of incorporating the drug to the injectable needle involves a step in which a polymerization reaction takes place.

The term "drug", refers to chemical or biological entities, including but not limited to, small molecules, DNA, RNA, proteins, peptides, viruses, virus-like particles, bacteria, protozoa, hormones and toxins, and extracts or fragments thereof, with therapeutic, prophylactic or diagnostic application in the field of animal and human health. The term "drug" therefore, includes medicines, vaccines, hormones, growth factors, and agents for biochemical or imaging diagnosis.

The term "injectable needle" refers to a monolithic needle-like object, preferably with a sharp end, and with a diameter smaller than 5 mm, preferably between 0.2 and 2 mm, a length of less than 20 mm, preferably between 1 and 10 mm, with an aspect ratio between 1 and 20, preferably between 2 and 10, and that are able to penetrate the skin and administer a drug with the help of an appropriate delivery device. This includes, without limitation, injectable needles illustrated in FIG. 1. The injectable needles of the present invention contain at least 20% in mass of the polymer resulting from a polymerization process carried out to incorporate the drug. In a preferred embodiment, without limitation, the injectable needle contains between 30% and 90% in mass of the polymer matrix resulting from the polymerization process. Liberation of the drug contained in the injectable needles of the present invention results from the total or partial resorption by dissolution, degradation or disintegration of the polymer matrix that constitutes the injectable needles once inserted into dermal, subcutaneous or muscle tissues.

The formulation of injectable needles involving a polymerization reaction of the present invention solves problems associated to previous approaches involving extrusion or moulding of aqueous mixtures of sugars and preformed polymers. This approach has several disadvantages, which include degradation of the contained drug during the conformation process, considerable shrinkage during the drying process of the preformed needle, and a final needle composition which lacks the required stiffness for percutaneous penetration.

The fabrication of injectable needles by polymerization of the present invention takes advantage of the contribution of polymerizable monomers and non-aqueous modifying agents to the fluidity of a drug-containing polymerizable paste or mixture devoid of water that can be easily moulded or extruded to the shape of an injectable needle.

Once moulded or extruded the paste can be made to set by polymerization into a stiff solid without loss of drug integrity and appreciable shrinkage. Furthermore, the present invention also incorporates procedures in which the integrity of the drug is preserved by its incorporation to the injectable needles as preformulated microparticles that are insoluble in the polymerizable paste or mixture. Resulting injectable needles contain the drug in the form of particles dispersed in the polymer matrix resulting from the polymerization reaction.

Components of the polymerizable paste or mixture used in the manufacture of the injectable needles of the present invention include:

a) Components of the polymerization reaction,
c) Drug,
d) Optional modifying agents.

Components of the polymerization reaction include one or more monomers which undergo a process of addition polymerization, initiated either chemically or photochemically, during conformation of the injectable needle. The monomers able to undergo addition polymerization reactions, also called polyaddition reactions, include, without limitation, anionic addition monomers and radical addition monomers. These can be either monomers that yield in linear polymers, or monomers that result in cross-linked polymers. Monomers yielding linear polymers include, without limitation: a) anionic addition monomers such as 2-cyanoacrilates, including alkyl 2-cyanoacrilates where the alkyl group are preferably methyl, ethyl, butyl or octyl, and b) radical addition monomers such as acrylates and methacrylates, including without limitation acrylic and methacrylic acids and/or alkaline, alkaline earth or ammonium acrylates and methacrylates, 2-hydroxypropyl acrylate, 2-hydroxypropyl methacrylate, (2-N,N-dimethylamino)ethyl acrylate), (2-N,N-diethylamino)ethyl acrylate), (2-N,N-dimethylamino)ethyl methacrylate), (2-N,N-diethylamino)ethyl methacrylate), glycerol acrylate, glycerol methacrylate, acrylamide, methacrylamide, N-iso-propylacrylamide, and/or vinylic monomers including, without limitation, N-vinylpyrrolidone. Monomers resulting in cross-linked polymers include, without limitation: a) diacrylates and dimethacrylates such as ethylene glycol diacrylate, ethylene glycol dimethacrylate, diethylene glycol diacrylate, diethylene glycol dimethacrylate, triethylene glycol diacrylate, triethylene glycol dimethacrylate, tetraethylene glycol diacrylate, tetraethylene glycol dimethacrylate, propylene glycol diacrylate, propylene glycol dimethacrylate, 1,4-phenylene diacrylate, 1,4-phenylene dimethacrylate, 1,4-butanediol diacrylate, 1,4-butanediol dimethacrylate, 1,6-hexanediol diacrylate, 1,6-hexanediol dimethacrylate; b) derivates of acrylamide such as N,N'-methylene-bis-acrylamide, N,N'-ethylene-bis-acrylamide, N,N'-hexamethylene-bis-acrylamide; and c) triacrylates such as 1,1,1-trimethylolpropane triacrylate and pentaerythritol triacrylate.

Linear polymers may sometimes and have poor initial stiffness and dissolve or degrade too fast in the physiological environment at the injection site. However, in the manufacture of injectable needles it may be desirable to have stiffer polymeric matrices with a controlled dissolution rate. In a preferred realisation of the present invention, the dissolution rate of the injectable needle is controlled through the addition of small amounts of cross-linking monomers which are incorporated to the components of the polymerisation reaction to obtain stiffer cross-linked polymers with reduced solubility.

On the other hand, these cross-linked polymers with reduced solubility may have the disadvantage of a low biodegradation rate in the physiological environment. In a yet preferred realisation of the present invention, the desired biodegradation or bioresorption rate of the injectable needles containing cross-linked polymers is accomplished by using hydrolysable cross-linking monomers as component of the polymerisation reaction. Such hydrolysable cross-linkers are monomers that contain functional groups able to undergo hydrolysis or cleavage by the action of chemical or enzymatic agents present in the physiological environment. Thus, the breakdown of the cross-linkers units renders the resulting polymer biodegradable or bioresorbable. These cross-linkers containing hydrolysable or cleavable functional groups include, without limitation, condensation oligomers of low molecular weight, carrying functional groups at their ends which are able to react via addition polymerization to originate a biodegradable cross-linked polymer. These cross-linkers include, without limitation, di- or triacrylates, or di- or trimethacrilates of polyethylene glycols, pluronics, and functionalised poly(hydroxyl alkanoates) and poly(lactide-co-glycolide)s.

The polymeric matrix resulting from the polymerization reaction can be formed from one or more addition monomers. The properties of the mixture that undergoes the polymerization reaction and of the resulting polymeric matrix may be additionally controlled by adjusting the nature and amount of the monomers included in the polymerization reaction. As illustrated in Examples 1 to 12, the choice of the adequate combination of monomers facilitates the manufacture of the injectable needles, avoiding the use of solvents and high temperatures that may degrade the contained drug and with sufficient strength to penetrate the skin and release the contained drug. As well, the biodegradation profile of the injectable needles can be modulated through the composition of the polymeric matrix, that is, the nature and amount of the monomers included in the polymerization reaction.

Other components of the polymerization reaction are initiators and catalysts which generate a reactive specie able to react with the monomer or monomers included in the polymerization reaction to start the addition reaction responsible for polymerization.

They can be intentionally added to the mixture or paste that undergoes the polymerization reaction or inherently present at the site where the reaction is conducted. Intentionally added initiators and catalysts may act through a thermal, chemical or photo-chemical process. In a preferred realisation of the present invention, low-temperature thermal initiators such as 2,2'-azobis(2-methylpropionitrile) and 1,1'-azobis(cyclohexanecarbonitrile), which are able to start the polymerization reaction at room temperature, can be employed. However, low-temperature thermal initiators require long reaction times that may be sometimes inappropriate for the manufacturing process of the injectable needles. Therefore, in other preferred realisation of the present invention, illustrated without limitation in Examples 1 and 5 the polymerization reaction is chemically initiated including a red-ox pair peroxide-amine of initiator (benzoyl peroxide) and catalyst (N,N-dimethylaminobenzyl alcohol) into the mixture that undergoes the polymerization reaction. However, the inclusion of a chemical red-ox initiation pair in the mixture to be polymerized limits the working time of the paste, which may be inconvenient for the manufacturing process of the injectable needles. Therefore, in other yet preferred realisation of the present invention, photochemical initiator and catalyst are included. The photochemical reaction responsible for the initiation of the polymerization proceeds only when the mixture of the polymerization reaction is irradiated with light of the required wavelength and power. Thus the working time of the mixture of components of the polymerization reaction is practically infinite. In a preferred realisation of the present invention, illustrated without limitation in Examples 6, 7, 9, 11 and 12, the photochemical initiator is (±)-camphorquinone, which is non toxic and cleared by the US Food and Drug Administration for use in biomedical devices. It forms a complex radical with tertiary amines when is irradiated with blue light of the proper intensity, thus avoiding the use of ultraviolet light as required by other photoinitiators of the radical polymerization, which prevents the possible decomposition or denaturing of the drug. On the other hand, in the same preferred realisation of the present invention, illustrated without limitation in Examples 6, 7, 9, 11, and 12, the catalyst used for photochemical is 2-(diethylamino)ethyl acrylate, a tertiary amine able to form the complex radical with (±)-camphorquinone and to participate as monomer in the free-radical polymerization, thus performing the double role of catalyst and monomer.

Furthermore, catalysts of the polymerization reaction can be inherently present at the site where the reaction is conducted. These catalysts can react with self-initiating monomers. In other preferred realisation, illustrated without limitation in Examples 1-4, 8 and 10, traces of water and other nucleophylic molecules or moieties inherently present in the mixture of the polymerization reaction are able to catalyse the polymerization of alkylcyanoacrylates.

In a preferred realization of the present invention, in addition to the drug, one or more modifying agents are incorporated to the polymerizable paste or mixture, either in suspension or in solution. The presence of these modifying agents in the polymerizable paste or mixture results in their incorporation to the final polymeric injectable needles resulting from the polymerization reaction.

Modifying agents that can be incorporated to the polymerizable paste or mixture include, without limitation, polymers, soluble particles, surfactants and reinforcing materials. Incorporation of polymeric modifying agents is illustrated without limitation in Examples 2, 7, 9, 11 and 12. These polymeric modifying agents include synthetic addition and/or condensation polymers and/or natural polymers. Synthetic addition polymers used as modifying agents include, without limitation, poly(N-isopropylacrylamide), poly(acrylamide-co-acrylic acid), poly(acrylic acid) and its alkaline salts, poly(2-hydroxypropyl acrylate), poly(2-hydroxypropyl methacrylate), and/or poly(N-vinylpyrrolidone). Synthetic condensation polymers used as modifying agents include, without limitation, poly(L-lactide), poly(glycolide), poly(DL-lactide-co-glycolide), poly[(−)3-hydroxybutyric acid], poly(caprolactam), poly(caprolactone), poly(ethylene glycol), poly(ethylene oxide-co-propylene oxide) and/or combinations thereof. Natural polymers used as modifying agents include, without limitation, cellulose, chitosan, starch, dextran, gelatin, collagen, fibronectin, hyaluronic acid, guar, agar, xanthan, agarose, alginic acid or alginate, and derivatives and/or combinations thereof. These polymeric modifying agents promote swelling and degradation of the formed polymer matrix in physiological conditions and contribute to the release of the drug contained in the resulting injectable needles.

Incorporation in the injectable needles of soluble particles and/or surfactants as modifying agents is illustrated, without limitation, in Example 3. Soluble particulate modifying agents include, without limitation, particles of soluble salts such as sodium hydrogencarbonate, potassium hydrogencarbonate, citric acid, sodium citrate, potassium citrate, lactic acid, calcium lactate, sodium lactate, potassium lactate, sodium hydrogen phosphate, potassium hydrogen phosphate, sodium dihydrogen phosphate, potassium dihydrogen and/or particles of soluble sugars such as monosaccharides, disaccharides and soluble derivatives of these, sugar alcohols, such as erythrose, threose, raffinose, ribose, arabinose, xylose, lyxose, allose, altrose, glucose, mannose, galactose, dihydroxyacetone, erythrulose, ribulose, xylulose, psychosocial, fructose, sorbose, tagatose, sucrose, lactose, maltose, isomaltose, trehalose, cellobiose, erythritol, treitol, arabitol, xylitol, ribitol, mannitol, sorbitol, dulcitol, iditol, maltitol, lactitol. After the injectable needle is percutaneously injected the soluble particles dissolve upon exposure to physiological conditions and generate pores in the polymer matrix. Creation of these pores results in a dramatic increase in surface area and a more rapid degradation or disintegration of the polymer matrix and release of the contained drug.

Surfactant modifying agents include, without limitation, anionic surfactants such as sodium dodecyl sulfate, salts of general formula RCOOX, where X=Na, K, $NH_4$, and R=hydrocarbon chain from 10 to 20 carbon atoms; cationic surfactants as cetrimide, benzalkonium chloride; swittierionic surfactants such as lecithin; non-ionic surfactants such as esters of sorbitol, ethoxylated derivatives of sorbitol esters, polyoxyethylated glycol monoethers, polymeric surfactants such as polyoxyethylene and polyoxypropylene copolymers. Use of surfactant modifying agents facilitates diffusion of physiological fluids to the interior of the polymer matrix and release of the drug from the polymeric injectable needles. Use of surfactant modifying agents can also facilitate the dispersion or dissolution of the monomers and other components prior to polymerization and conformation of the injectable needles. The use of surfactants as modifying agents may also facilitate incorporation of the monomer mixture into the appropriate moulds or facilitate extrusion processes prior to polymerization.

The choice of modifying agents incorporated into the solution of monomers allows for the design of injectable needles with different hardness and rigidity, rate of degradation or drug release of the injectable needle.

In another embodiment of the present invention, illustrated without limitation in Examples 4 and 9, the injectable needles incorporate reinforcing modifying agents in the form of particles or fibres that contribute to a greater strength and/or hardness of the injectable needles. These particles or fibres are homogeneously dispersed in the polymer matrix resulting in a composite material in which the polymer matrix constitutes the continuous phase. Reinforcing modifying agents can be, without limitation, metal oxides, bioglasses of varying composition, salts of calcium or other metals, preferably carbonates, phosphates, silicates, aluminates or zirconates. The aspect ratio of the reinforcing fibres or particles is between 0.5 and 100, preferably between 1 and 20. The volume fraction of the reinforcement modifying agent incorporated in the injectable needles is between 0.03 and 0.5, preferably, and without limitation, between 0.05 and 0.3. The particles or fibres used as reinforcing modifying agents can be incorporated without modification to the polymer matrix or their surface can be can be previously treated with coupling agents to improve their compatibility with the polymer matrix to increase their reinforcement action. Coupling agents for surface treatment of the reinforcing modifying agents include, without limitation, silanes and organic acids and their salts. Manufacture of the injectable needles involves a first step in which the drug, the components of the polymerization reaction and the optional modifying agents are thoroughly mixed to form a paste and a second step in which the drug-containing polymerizable paste or mixture is made to polymerize to produce a solid polymer matrix containing the drug. As represented without limitation in FIGS. 1 and 2, the drug can be present in different forms in the resulting polymer matrix. In a particular embodiment of the present invention the drug is in solid solution in the polymer matrix. Injectable needles resulting from the polymerization of mixtures in which the drug is dissolved in the components of the polymerization reaction and homogeneously dispersed in the final polymeric injectable needle are illustrated, without limitation, in Examples 2-5. Dissolution of the drug in the mixture containing monomers and other reaction components may be facilitated by use of monomers with adequate polarity, use of solvents and/or surfactants. Dissolution of the drug in the components of the polymerization reaction can result in their degradation and loss of biological activity. Furthermore the polymerization reaction itself can contribute to loss of biological activity of the contained drug. This can be partially alleviated by incorporation of surfactants and other agents, such as proteins, that may in some way associate with the drug and provide protection against the polymerization process.

In a preferred realization of the invention, exposure and potential degradation of the drug prior and during the polymerization reaction is greatly reduced, if not eliminated, by incorporation of the drug as microparticles, larger fragments or as a monolithic shape longitudinal to the shape of the injectable needle. In this embodiment, preference is given to monomers, solvents and other components of the polymerization reaction in which the drug is not soluble. Addition of surfactants to the components of the polymerization reaction may contribute to reduce direct contact of the drug particles in suspension with the components of the polymerization reaction and minimize its degradation. Yet in a preferred embodiment of the present invention, illustrated without limitation in Examples 6-12, the drug is preformulated into dry solid particles which are insoluble in the components of the polymerization reaction. The preformulated particles made to contain the drug have a preferred diameter between 0.02 and 500 microns, more preferably between 0.1 and 100 microns. Incorporation of the drug to the components of the polymerization reaction in the form of preformulated dry solid drug-containing particles which are insoluble in the components of the polymerization reaction results in composite injectable needles in which the continuous phase is made from the polymer resulting from the polymerization reaction and a discontinuous phase formed by the drug-containing preformulated microparticles. Preformulation of the drug into microparticles insoluble in the polymerization reaction components can be accomplished using commonly used excipients in the field of drug formulation and stabilization. Example excipients in the formulation of drug-containing microparticles include, without limitation, sugars, sugar alcohols, amino acids, proteins, or combinations of them, between preferred stabilizing agents include mannitol, sucrose, dextrose, xylitol, erythritol, fructose, mannose, maltose, maltotriose, lactose, lactobiosa, arabinose, xylose, ribose, galactose, rabbis, trehalose, calcium lactate, ectoin, hydroxyectoin, albumin, ovalbumin, collagen, casein, proline, arginine, dextran, alginates, hyaluronic acid. Preformulated drug-containing particles may incorporate surfactant agents that contribute to the dissolution of the drug during the preformulation process or provide a coating to the drug-containing particle which may even take the form of a capsule. The presence of surfactant agents on the surface of the drug-containing particle facilitates dispersion of particles in the components of the polymerization reaction and may prevent premature polymerization of the components of the polymerization reaction by avoiding direct contact of monomers with potential initiator radicals on the surface of the drug-containing particle. Preformulation of drug-containing particles can be accomplished by commonly used processes in the field of drug formulation such as vacuum-drying or lyophilization and subsequent pulverization, spray-drying, electrospinning, granulation, etc. Incorporation of the drug to preformulated particles provides long-term stability and avoids potential degradation of the active drug resulting from direct contact with the components of the polymerization reaction. Furthermore, incorporation of the drug to injectable needle in form of preformulated drug-containing particles provides a means for modulating the drug release and degradation profile of the injectable needles. Drug-containing particles which rapidly dissolve in physiological conditions facilitate drug release from the resulting injectable needles in short time frames while less soluble drug-containing particles retard drug release from the injectable needles. Particle load also has a determinant effect on drug release and injectable needle degradation profile. Incorporation of soluble particles above 20%, and preferably above 30% in weight of the continuous polymeric phase favour rapid release of the contained drug and seriously compromise the integrity of the injectable needle after injection favouring its disaggregation and degradation.

It can often be desirable that the injectable needles have a composition that causes a moderate local immune response in the receiving organism in order to enhance the biological action of the drug. As is illustrated without limitation by Examples 7 and 11, this is especially desirable in the administration of vaccines. To that end the injectable needles can be made to contain modifying agents with adjuvant activity which include, without limitation, calcium phosphates, aluminium phosphates, aluminium hydroxide, calcium phosphate, saponins, proteasomes, immunostimulating complexes (ISCOM), and mycolic acid and mycolates, pyridina, vitamin A, vitamin E, halides, dimethyldioctadecylammonium (DDA), muramyl dipeptide and tripeptide, monophosphoryl lipid A, monofosforilado, trehalose dimycolate, CpG oligodeoxynucleotide motifs, liposomes, cytokines, glucans, dextrans, lentinan, glucomannan, galactomannans, acemanane, interferon, interleukins, virosomes, bacterial toxins, levamisole, etc. Immune response enhancing adjuvant agents may be incorporated in solution, suspension, in the form of solid particles, microparticles, nanoparticles, and with stabilizing agents. Moreover, the polymers and modifying agents used in vaccine formulations in the form of injectable needles of the present invention can help magnify the immune response.

Solvents can be added to the components of the polymerization reaction or to the polymerizable paste or mixture to facilitate their intimate mixture or dissolution. The incorporation of solvents, as modifying agents, to the components of the polymerization reaction can also facilitate the incorporation of the resulting mixture to a mould or its extrusion through a nozzle. To avoid potential degradation of the drug by direct contact with the solvent, preferred solvents are those that do not dissolve the drug particles or preformulated drug-containing particles. Examples of these solvents include, without limitation, acetone, chloroform, dimethylsulfoxide, methyl acetate, ethyl acetate, n-propyl acetate, iso-propyl acetate, n-butyl acetate, iso-butyl acetate, n-hexane, n-heptane, dimethylformamide, dichloromethane, 1,2-propanediol, n-propanol, iso-propanol, n-butanol, iso-butanol, etc. These solvents are incorporated to the components of the polymerization reaction and removed completely by evaporation following conformation of the injectable needle. The relative amount of solvents that can be added to the components of the polymerization reaction is limited by the dimensional changes associated with evaporation during the manufacture of the injectable needles. Relative amounts of solvents that result in dimensional changes in excess of 40% are not favoured in the manufacture of injectable needles of the present invention.

Injectable needles of the present invention can be manufactured by different means. In a particular realization of the present invention manufacture of the injectable needles is carried out by through mixing of the components of the polymerization reaction, optional modifying agents and the drug in any of its forms, to form a polymerizable paste or semisolid mixture. The resulting drug-containing polymerizable paste or mixture can then shaped to the form of an injectable needle by various procedures including, without limitation, mould casting, injection moulding, extrusion, press and die arrangements, compression or combinations of thereof, and then made to harden by polymerization. Manufacture of injectable needles by mould casting is illustrated, without optional modifying agents and drug in any of its forms are mixed into a paste which is poured or injected into a needle shaped moulds where polymerization process takes place to produce a hard solid injectable needle. Manufacture of injectable needles by extrusion is illustrated, without limitation, by Examples 2, 4, 6, and 12. The procedure involves mixture of the different components of the polymerization reaction, modifying agents, and drug in any of its forms, into a plastic paste which on application of pressure is extruded trough a nozzle with the cross section of the desired injectable needle. The cable-like product of the extrusion process can then be induced to polymerize and cut into appropriate lengths to form the injectable needles.

Alternatively, in another realization of the present invention the drug-containing polymerizable paste can be arranged into sheets and made to harden by polymerization. Injectable needles can then be cut out from the polymerized sheets by press and die arrangements. Manufacture of injectable needles by press and die arrangements is illustrated, without limitation, by Examples 8 and 10.

Alternatively, in yet another realization of the present invention, solid components can be compressed or compacted by press and die arrangements and subsequently impregnated by a solution containing monomer and, optionally, other components of the polymerization reaction, and made to polymerize. Example 10 illustrates, without limitation, manufacture of injectable needles by compression of a powder material into a mould by applying pressure, and subsequent impregnation of the compressed material with a monomer or mixture of monomers and/or polymers, which is then made to polymerize to provide the compressed powder with the necessary stiffness to form an injectable needle.

The combination of two or more of the basic procedures for manufacturing the injectable needles of the present invention is illustrated, without limitation, in Example 11, which incorporates a press and mould casting procedures. In a preferred form of the present invention, the mould in which the polymerization reaction takes place and which gives the injectable needle its final shape and size is designed to house the injectable needle in the injector or pusher device for its percutaneous delivery. Maintaining the injectable needle in its mould after polymerization facilitates further manipulation of the cast injectable needle and loading on to the injector device. Furthermore the injectable needle can be manufactured directly into the injector or pusher device, or one of its parts, to avoid the need for further manipulation.

In one embodiment the injection needles are cut to desired length while still contained in the mould. As illustrated, without limitation, in Examples 3 to 5, an oblique cut of the mould containing the injectable needle results in a sharp end that provides the needle with greater penetration power. Two blades placed at an angle against their sharp ends may also be used to provide the injectable needle with a sharp triangular tip.

A common element in the manufacturing process of the injectable needles of the present invention is the polymerization reaction that provides the injectable needles with the required hardness and rigidity for their percutaneous injection by simple injector or pusher devices illustrated, without limitation, in FIG. 3. Application of polymerization processes in the manufacture of injectable needles according to the present invention avoids high temperatures and permits the use of conditions in which the integrity of the contained drug is preserved. Furthermore, an advantage in the use of polymerization reactions in the manufacture of the injectable needles is the avoidance of shrinkage and changes of shape upon polymerization. Avoidance of shrinkage facilitates moulding and extrusion procedures in which the size and shape of the injectable needle is determined prior to polymerization while the mixture of components is still easily workable. Yet, furthermore, polymerization processes in which the polymerization reaction does not affect the contained drug, be it because it does not take part in the reaction or because it is previously preformulated, are essentially devoid of water and the detrimental effects on drug stability that are often associated with the presence of water.

Manufacturing processes of the present invention incorporating a polymerization reaction facilitate the incorporation of drug stabilizing agents. In particular, manufacturing processes involving preformulation of the drug into dry solid particles and subsequent incorporation into a polymerizable paste or mixture is very effective in preserving the integrity of sensitive drugs during manufacture of the and provide long term stability at room temperature of the drug contained in the injectable needle. This is of particular interest in the formulation of drugs with application in situations where cold storage is not possible.

Another aspect of the present invention relates to a method for the manufacture of injectable needles as defined above which comprises a polymerization reaction.

In another embodiment, the invention refers to a method of obtaining the injectable needles defined above wherein the polymerization reaction is a polyaddition reaction.

In another embodiment, the invention refers to a method of obtaining the injectable needles defined above which further comprises an initiator and a catalyser.

In another embodiment, the invention refers to a method of obtaining the injectable needles defined above wherein the catalysis of the polyaddition polymerization reaction is chemical.

In another embodiment, the invention refers to a method of obtaining the injectable needles defined above wherein the catalysis of the polyaddition polymerization reaction is photochemical.

In another embodiment, the invention refers to a method of obtaining the injectable needles defined above which further comprises a polymerizable paste or mixture that includes the components of the polymerization reaction and a drug.

In another embodiment, the invention refers to a method of obtaining the injectable needles defined above wherein the drug is in solution in the polymerizable paste or mixture.

In another embodiment, the invention refers to a method of obtaining the injectable needles defined above wherein the drug is dispersed in the polymerizable paste or mixture.

In another embodiment, the invention refers to a method of obtaining the injectable needles defined above wherein the drug is dispersed in the polymerizable paste or mixture as preformulated drug-containing particles.

In another embodiment, the invention refers to a method of obtaining the injectable needles defined above wherein the polymerizable paste or mixture contains modifying agents.

In another embodiment, the invention refers to a method of obtaining the injectable needles defined above wherein the modifying agents present in the polymerizable paste or mixture are preformed polymers.

In another embodiment, the invention refers to a method of obtaining the injectable needles defined above wherein the modifying agents present in the polymerizable paste or mixture are soluble particulate modifying agents.

In another embodiment, the invention refers to a method of obtaining the injectable needles defined above wherein the modifying agents present in the polymerizable paste or mixture are surfactants modifying agents In another embodiment, the invention refers to a method of obtaining the injectable needles defined above wherein the modifying agents present in the polymerizable paste or mixture are reinforcing modifying agents that contribute to increased hardness or rigidity.

In another embodiment, the invention refers to a method of obtaining the injectable needles defined above wherein the modifying agents present in the polymerizable paste or mixture have adjuvant activity.

In another embodiment, the invention refers to a method of obtaining the injectable needles defined above wherein the polymerization reaction takes place in a mold.

In another embodiment, the invention refers to a method of obtaining the injectable needles defined above wherein the mold is incorporated in a delivery device for percutaneous administration.

In another embodiment, the method further comprises an extrusion process.

Another aspect of the present invention relates to an injectable needle obtainable by a method as defined above.

Furthermore, the present invention covers all the possible combinations of the particular and preferred embodiments described above.

Thus, another aspect of the present invention relates to a kit comprising:
- an injectable needle as defined above or an injectable needle obtainable by a method as described above; and
- a delivery device.

The formulations and procedures described in the present invention enable the effective incorporation of drugs to injectable needles with enough rigidity and hardness to be injected percutaneously by simple pusher or injector devices. These injectable needles are of medical and veterinary application, and are of special interest in situations where the use of hypodermic needles and perishable drugs that require refrigeration and reconstitution with sterile water represent a serious health problem.

Another aspect of the present invention relates to the use of the injectable needles of the present invention in the preparation of a drug. A preferred embodiment of this aspect of the invention refers to the use of the needle of the invention in the preparation of a drug for subcutaneous administration.

Thus, another aspect of the present invention relates to an injectable needle as defined above or an injectable needle obtainable by a method as defined above or any kit as defined above for use in therapy wherein said injectable needles and said kit are adapted for percutaneous administration.

Another aspect of the present invention relates to an injectable needle as defined above or an injectable needle obtainable by a method as defined above or any kit as defined above for use in the treatment, prevention or diagnosis of a human or animal disease.

Another aspect of the present invention relates to an injectable needle as defined above or an injectable needle obtainable by a method as defined above or any kit as defined above for the administration of therapeutic agents, preferably therapeutic vaccines, antivirals, growth factors, gene therapies, antiinflammatories, analgesics, immune modulators, desensitizers and hormones.

Another aspect of the present invention relates to an injectable needle as defined above or an injectable needle obtainable by a method as defined above or any kit as defined above for the administration of human prophylactic vaccines, preferably hepatitis B, hepatitis A, meningococcus, pneumococcus, rabies, influenza, polio, measles, mumps, rubella, varicella, botulinum, dengue, tuberculosis, HIV, malaria and their combinations thereof.

Another aspect of the present invention relates to an injectable needle as defined above or an injectable needle obtainable by a method as defined above or any kit as defined above for the administration of veterinary vaccines and diagnostics.

Another aspect of the invention relates to drug delivery devices that contain the injectable needles of the present invention. There are numerous injector or pusher type devices for the delivery of injectable needles known in the state of the art. Devices for the delivery of injectable needles include simple devices which may be disposable, devices for repetitive administration of injectable needles, catheter type delivery devices and designs in which the injectable needle may be attached to the end of rod that facilitates their injection.

The combination of the injectable needle and the delivery device constitutes the kit of parts required for the administration of the drug, so that another aspect of the invention relates to the use of an assembly comprising injectable needles of the present invention and a pusher or injector device in the manufacture of a medical device. In a preferred embodiment of this aspect of the invention, the drug is administered percutaneously, either intradermally, subcutaneously or intramuscularly.

The following figures and examples illustrate the scope of the invention.

EXAMPLES

Example 1

Injectable Needles Incorporating Linear Polymers and Combinations Thereof

Figure 1:
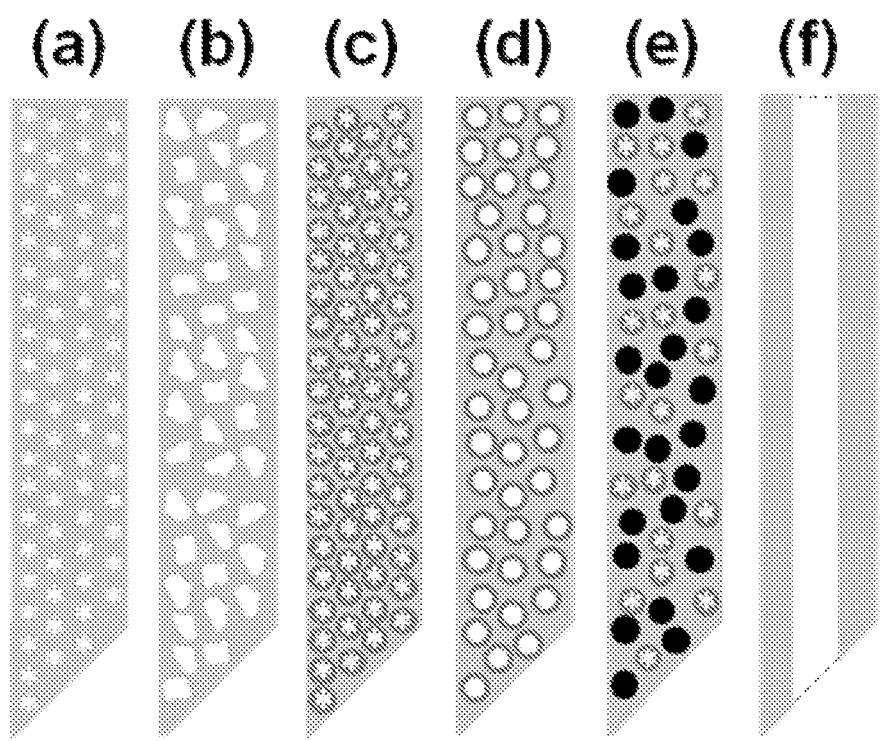
FIG. 1: Representation of some of the possible formulations of injectable needles, (a)-(f), in which the active drug or vaccine is represented by the symbol (*). In (a) the active is dissolved in the matrix that makes up the needle, in (b) the active is dispersed into particles or granules in the matrix, in (c) the active is contained in nano- or micro-particles of made of stabilizer or acceptable excipient, in (d) the active is contained in nano- or micro-capsules; in (e) the needle includes particles that contribute to the hardness of the needle or modify their release profile; and in (f) the drug forms a monolith that is incorporated into the injectable needle.
Figure 2A:
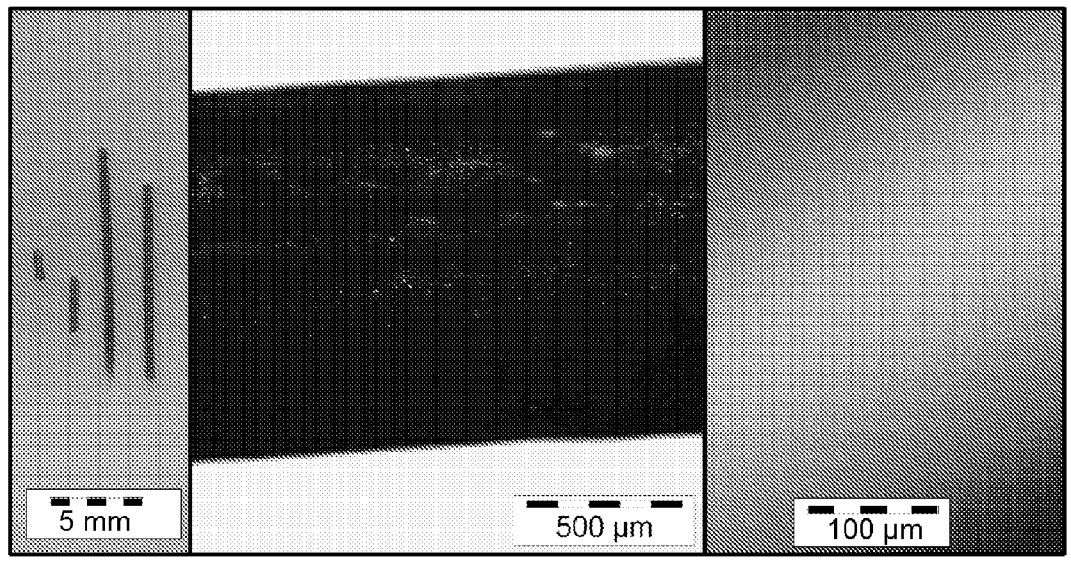
FIG. 2: Micrographs of injectable needles containing a drug, a) wherein the drug is in solid solution in the polymer matrix, and b) wherein the drug is dispersed in the polymer matrix in the form of pre-formulated microparticles.
Figure 2B:
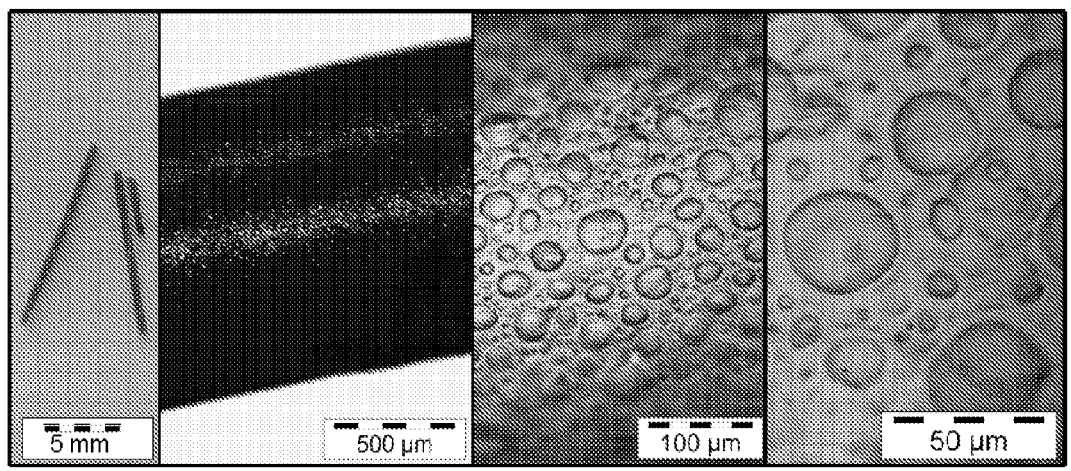
Figure 3A:
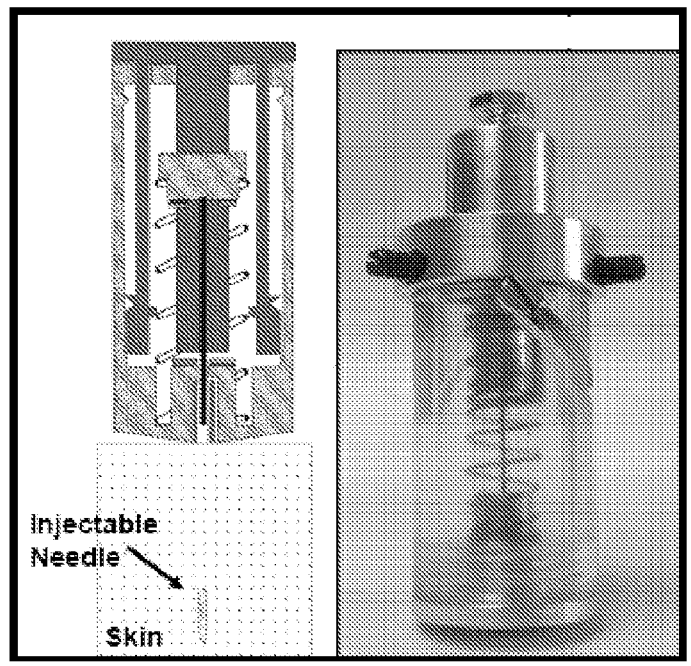
FIG. 3: Example pusher or injector delivery device. (a) Experimental injector prototype device for percutaneous administration of injectable needles, (b) Entry orifice and final location of the injectable needle after using the injector prototype device on an apple as a model of tissue.
Figure 3B:
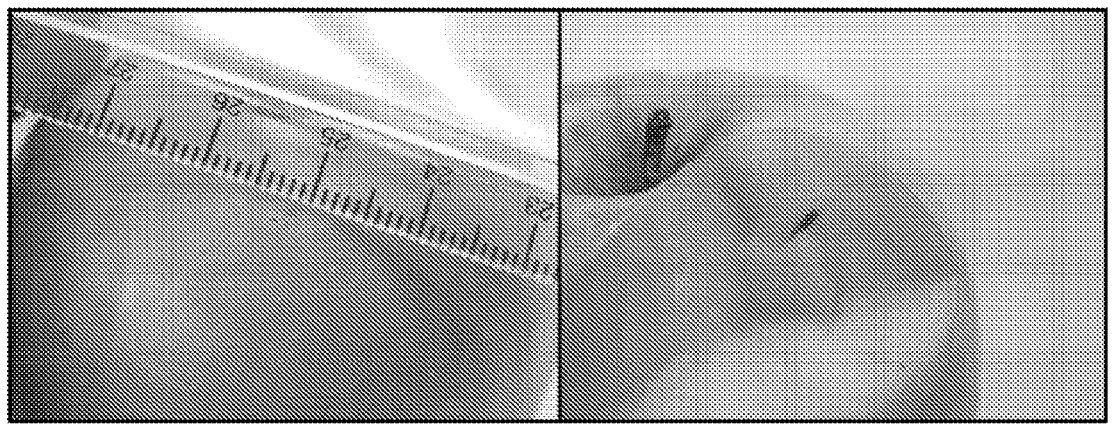

In the manufacture of injectable needles 250 mg of Coomassie Blue R-250 powder used as a model drug are mixed with 1 ml of the monomer or monomer mixtures listed in Table 1. For mixtures containing radical addition monomers, benzoyl peroxide (3 wt. % with regard to monomer) is added as initiator and N,N-dimethylamine benzyl alcohol (0.5 wt. % with regard to monomer) as co-initiator. The resulting polymerizable pasty mixture is introduced by aspiration into 1 mm inner diameter Teflon tube and left to polymerize for 24 hours. Once the polymerization process is completed the Teflon tube is cut into 3 mm long sections. The injectable needles obtained are loaded into an appropriate pusher or injector delivery device as shown in FIG. 3. Actuation on the delivery device forces penetration of the injectable needle in a tissue model. To determine liberation of the model active, Injectable needles were incubated in 5 ml of buffered saline (pH 7.4) for one week at 37° C. At different time intervals, 500 μl samples were taken and replaced by fresh the same volume of fresh saline. Absorbance at 590 nm of the obtained sample is determined the amount of model drug calculated against a calibration curve. After one week the dry mass of the remaining material is determined and the weight loss relative to the original injectable needle sample is calculated. Incorporation of different monomers results in different profiles of model drug release and degradation of needle injections.

TABLE 1

| Monomers | Release (% drug recovery) | Degradation (% mass loss) |
| --- | --- | --- |
| ANIONIC ADDITION MONOMERS | | |
| Methyl-2-cyanoacrylate | +++ | +++ |
| Ethyl-2-cyanoacrylate | +++ | ++++ |
| n-Butyl-2-cyanoacrylate | ++ | ++ |
| n-Octyl-2-cyanoacrylate | ++ | ++ |
| FREE-RADICAL ADDITION MONOMERS | | |
| Acrylic acid | +++++ | +++++ |
| Acrylamide | +++++ | +++++ |
| N-iso-propylacrylamide | +++++ | ++++ |
| Methacrylic acid | +++++ | ++++++ |
| 2-Hydroxypropyl methacrylate | +++ | +++ |
| 2-Hydroxyethyl methacrylate | +++ | +++ |
| 2-(N,N-Dimethylamino)ethyl methacrylate | ++++ | ++++ |
| Methacrylamide | ++++ | ++++ |
| N-vinyl-2-pyrrolidone | +++++ | +++++ |
| N,N'-Methylenebisacrylamide | ++++ | + |
| Diethylene glycol diacrylate | +++ | + |
| 1,1,1-Trimethylolpropane triacrylate | ++ | + |
| Triethylene glycol dimethacrylate | + | + |
| 2,2-Bis[4-(2-hydroxy-3-ethacryl-oxypropoxy)phenyl]propane (Bis-GMA) | + | + |
| Pentaerythritol triacrylate | + | + |
| ADDITION MONOMER MIXTURES | | |
| Ethyl-2-cyanoacrylaten/Butyl-2-cyanoacrylate (1:1) | +++ | ++ |
| Acrylic acid/N-vinyl-2-pyrrolidone (1:1) | +++++ | +++++ |
| Triethyleneglycol dimethacrylate/Bis-GMA/2-(N,N-Dimethylamino)ethyl methacrylate (1:1:1) | ++ | + |

Example 2

Injectable Needles Incorporating Polymeric Modifying Agents

For the incorporation of polymeric modifying agents into the composition of the injectable needles, 80 mg of poly(DL-lactide-co-glycolide) [50:50; MW ~12,000-16,000] or poly-caprolactone [MW 43,000-50,000], as polymeric modifying agents, are added to 280 μl of ethyl acetate. To the resulting solution 1 ml of ethyl cyanoacrylate monomer and 250 mg of Coomassie Blue R-250 powder as a model drug are added. Dissolution of the polyDL-lactide co-glycolide or polycaprolactone polymeric modifying agents in ethyl acetate facilitates their dissolution in the monomer to form a fluid pasty mixture. The polymerizable paste mixture is homogenized, degassed and extruded in a 1 mm internal diameter Teflon tube of and allowed to polymerize for 24 hours to produce a poly(ethylcyanoacrylate) containing polyDL-lactide co-glycolide or polycaprolactone as polymeric modifying agents. Once the polymerization process is concluded the Teflon tube is cut into 3 mm lengths to produce injectable needles. Incorporation of polymeric modifying agents to the final composition leads to solid injectable needles that take up fluid and swell upon exposure to aqueous media and have a more rapid disaggregation rate in simulated physiological fluid.

Example 3

Injectable Needles Incorporating Soluble Particles and Surfactants as Modifying Agents For the incorporation of soluble particles and surfactant modifying agents in injectable needles, 50 mg of 25 µm mannitol particles are dispersed as soluble particulate modifying agents, and 250 mg of Coomassie Blue R-250 powder are dissolved as a model drug in 1 ml octyl-2-cyanoacrylate monomer to produce a workable polymerizable paste. A similar paste was made to incorporate 10 µL of polysorbate-20 surfactant modifying agent as an additional component. Polymerizable paste mixtures are homogenized and injected by vacuum in a Teflon tube of 1 mm internal diameter and left to polymerize for 24 hours. Once the polymerization concludes and the pastes have hardened, the Teflon tube is cut to 3 mm lengths alternately at 45° or 90° to produce sharp pointed injectable needles. The resulting solid injectable needles are compared to needles prepared by the same procedure but in the absence of soluble particles and surfactant modifying agents. For this, the injectable needles are incubated in 5 ml of buffered saline (pH 7.4) for one week at 37° C. Incorporation of soluble particles to the injectable needles results in solid injectable needles that after injection develop a macroporosity resulting from the dissolution of the soluble particles and a faster release of the drug. Addition of the surfactant modifying agent provides a greater fluidity to the pasty mixture containing the monomer, soluble particles and model drug, and a faster release of drug model.

Example 4

Injectable Needles Incorporating Reinforcing Modifying Agents

Coomassie Blue R-250 powder as a model drug, 25 mg is dissolved in a mixture of 180 µl butyl cyanoacrylate monomer and 2 ml of Pluronic® F-68 as a surfactant modifying agent. For the incorporation of reinforcing modifying agents that increase the stiffness of the injectable needles, 0, 20 and 40 mg of Bioglass® (calcium sodium silica phosphate glass milled to an average particle size of 2 µm), are incorporated to the resulting mixture to increase stiffness and penetrability of the injectable needle. The polymerizable paste is extruded under pressure into a 1 mm internal diameter Teflon tube mould and allowed to polymerize and harden for 24 hours. The Teflon tubular mould containing the hardened mixture is cut to 3 mm lengths, alternately at 45° or 90° angles, to form injectable needles which are easily removed from the mould. Incorporation of reinforcing modifying agents, such as powdered Bioglass®, to the final composition of the injectable needle results in injectable needles with significantly increased stiffness and penetrability than those prepared without Bioglass®.

Example 5

Injectable Needle Incorporating a Drug Dispersed in the Polymer Matrix

For incorporation of a bactericin vaccine, as a model of drug, homogeneously dispersed in the injectable needles, 50 mg of the bactericin are dissolved in a mixture of 200 µl of acrylic acid and 300 µl of diethylene glycol diacrylate. To the resulting solution 7.5 mg of N,N-dimethylamino benzyl alcohol and 7.5 mg benzoyl peroxide are added and mixed into a fluid paste. The resulting polymerizable paste is extruded by suction into 1 mm internal diameter tubular Teflon moulds and made to polymerize and harden for 24 hours at room temperature. The tubular mould is cut into 3 mm long sections, alternately at 45° or 90° to produce a sharp and a blunt end in each of the needles. Resulting injectable needles are removed from the mould. Scanning electron microscope demonstrated that the drug is in solid solution in the polymer matrix that constitutes the injectable needle. As an injectability test needles contained in their Teflon mould were loaded in an injector delivery device. Action of the delivery device permitted the injection of the injectable needle in a skin tissue model. Incubation of the injectable needles in 5 ml of buffered saline (pH 7.4) for one week at 37° C. demonstrated release of most of the bactericin originally incorporated into the needle.

Example 6

Injectable Needles Containing a Drug in Preformulated Solid Microparticles Dispersed in a Polymeric Matrix Water soluble microparticles with particle size between 1 and 10 µm and a final dry content of 98 wt. % trehalose, 2 wt. % of poly(N-vinylpyrrolidone), and 100 mU/g of β-galactosidase as a model drug, are pre-formulated by spray drying. A polymerizable paste is prepared from 200 mg microparticles and 1 mL of a mixture of diethyleneglycol diacrylate (70 wt. %), 2-hydroxyethyl methacrylate (29 wt. %), (2-N,N-dimethylamino)ethyl methacrylate (0.7 wt. %) and camphorquinone (0.2 wt. %). The polymerizable paste is extruded into a transparent silicone tube of 1 mm inner diameter and irradiated with blue-violet light for 10 minutes to promote photo-polymerization. The silicone tube containing the polymerized material is cut into 7 mm length sections. The injectable needles are removed from the tube and incubated at 4° C. and 45° C. for 4 weeks.

Figure 4:
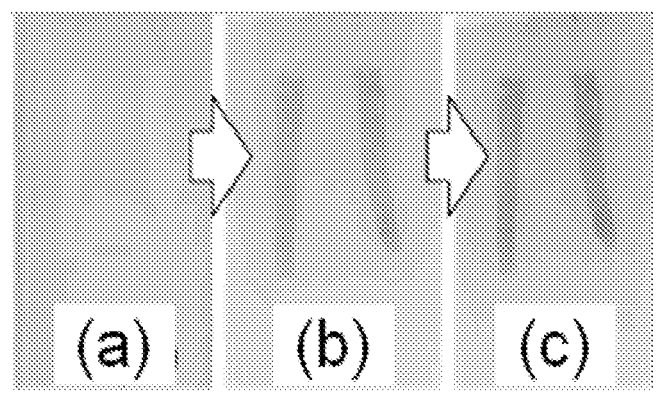
FIG. 4: Photos of two injectable needles, prepared as illustrated in Example 6, that incorporate β-galactosidase in their formulation and have been injected in an agarose gel containing 100 μg/ml X-Gal. Prior to injection the injectable needles were maintained for 4 weeks at 4° C. (needle on the right) or at 45° C. (needle on the left). (a) Injectable Needles immediately after injection in the gel, (b) Injectable Needles 24 hours after injection in the gel, and (c) Injectable needles 48 hours after injection in the gel. The blue colour of increasing intensity observed in the agarose gel shows the enzymatic activity of 6-galactosidase on X-Gal substrate and the absence of an appreciable difference between the needle previously maintained at 4° C. and 45° C.

To evaluate β-galactosidase activity needles were injected into a 2% agarose gel containing 100 µg/ml of X-Gal (5-bromo-4-chloro-3-indolyl-β-D-galactopyranoside) and maintained at 37° C. In a few minutes a blue colour is observed in the vicinity of the injectable needles due to the release of β-galactosidase and transformation of the X-Gal substrate by the β-galactosidase enzymatic action, as illustrated in FIG. 4. No significant difference in the ability to induce a colour change from needles incubated at 4° C. and 45° C. indicates effective stabilization of the model drug.

Example 7

Injectable needles incorporating a vaccine and an Adjuvant Preformulated in Solid Microparticles Dispersed in a Polymeric Matrix Poly(D,L-lactide-co-glycolide) 50:50, 140 mg; camphorquinone, 3.5 mg, acrylic acid, 650 mg, diethyleneglycol diacrylate, 950 mg, (2-N,N-dimethylamino)ethyl methacrylate, 140 mg, are thoroughly mixed. Optionally 1 mg of a synthetic oligonucleotide containing CpG is added to the mixture as adjuvant agent.

Microparticles consisting of 90.5% trehalose, 2% polyvinylpyrrolidone, and 7.5% of hepatitis B surface antigen (HBsAg), as a model drug, and particle size between 1 to 10 μm are produced by spray-drying. The microparticles, 500 mg, are thoroughly dispersed into the mixture of polymers, monomers, and initiator, and the resulting paste is injected into 1 mm internal diameter transparent silicone tube as a mould. The mixture is made to polymerize by irradiation with blue-violet light for 10 minutes. The silicone tube with polymerized material is cut into 10 mm long sections to provide with the injectable needles.

Needles, with (A) and without CpG (B) were implanted in BalbC C3H mice, 9 mice per experimental group, and antibody titers in blood against HBsAg determined by ELISA after 28 days compared with mice vaccinated with Recombivax HB (Merck) (C) as shown in Table 3. All mice showed seroprotection with levels over 10 U/I. Incorporation of CpG to the injectable needles as an adjuvant modifying agent resulted increased antibody titres.

TABLE 2

| Sample | Anti HBsAb Antibody Titer (U/l) | S. Deviation (IU/L) |
|---|---|---|
| A) Pre-formulated HBsAb containing particles | 43 | 8 |
| B) Injectable Needles 4° C. | 36 | 8 |
| C) Injectable Needles 37° C. | 38 | 6 |
| D) Recombivax HB ® | 41 | 8 |
| E) Recombivax HB ® at 37° C. | 21 | 6 |

Example 8

Injectable Needles Incorporating a Drug as a Longitudinal Monolith

Drug-containing water soluble microparticles consisting of 90% trehalose, 9% calcium lactate, 1% polyvinylpyrrolidone, and 100 mU/g of (3-galactosidase as a model drug, are prepared by spray drying. Microparticles are pressed at 50 MPa in a 1.5×1.5×10 mm steel die to form a monolithic rod. The obtained rods are inserted into 12 mm length and 2.2 mm diameter Teflon tubular moulds. A solution of 10% of polycaprolactone in methyl cyanoacrylate is prepared and dispensed into the Teflon tubes containing the monolith to fill the clearance. The system is left to polymerize for 24 h. The resulting 12 mm length and 2.1 mm diameter cylindrical injectable needles are removed from their moulds and incubated dry at 4° C. and 45° C. for 4 weeks to determine integrity of the contained β-galactosidase. To determine β-galactosidase activity injectable needles are incubated at in 5 ml of buffered saline (pH 7.4) for 3 hrs after which 92±4% of β-galactosidase enzymatic activity is observed by X-Gal colorimetric determination compared to that obtained from the pressed monolith stored in equal conditions.

Example 9

Injectable Needle Containing Preformed Polymeric Modifying Agents and Manufactured by Extrusion and Photopolymerization Drug-containing water soluble microparticles consisting of 75% trehalose, 18.8% of calcium lactate, 3.4% bovine serum albumin, 1.9% Pluronic F-68 and 0.4% β-galactosidase (151 U/mg) as a model drug, with a particle size between 1 to 10 μm, are prepared by "spray drying". Poly(N-vinylpyrrolidone), 400 mg; powdered hydroxyapatite, 260 mg, and microparticles, 100 mg, are thoroughly mixed. On the other hand, acrylic acid, 120 mg; camphorquinone, 10 mg; and (2-N,N-dimethylamino)ethyl methacrylate, 120 mg, are thoroughly mixed. The powder and liquid components are thoroughly mixed into a homogeneous fluid workable paste. The paste is fed to the pump chamber of a high-pressure syringe pump fitted with a 0.686 mm interior diameter needle. The paste is injected into a 0.8 mm cylindrical silicone mould with a sharp end and polymerized by irradiation with filtered halogen light (λ=440-480 nm, 1,400 mW/$cm^2$) for 10 min. The 3-4 mm in length injectable needles formed by the injection moulding are loaded on to a simple injector delivery device for injection into a porcine skin model. Immersion of the needles into 5 ml of buffered saline (pH 7.4) at 37° C. for 3 days followed by an X-Gal assay on the saline resulted in a colour change indicative of liberation of enzyme activity.

Example 10

Injectable Needle Manufactured by a Press and Punch Arrangement

Microspheres consisting of 75.6% trehalose, 21.6% calcium lactate, 2.2% of the surfactant Pluronic F127 and 0.6% bovine serum albumin, as a model drug, and particle size between 1 to 10 μm are produced by spray-drying. On the other hand, 140 mg of poly(D,L-lactide-co-glycolide) 50:50 are dissolved in a mixture of 450 mg of ethyl acetate and 1800 mg of ethyl cyanoacrylate. The liquid and powder are thoroughly mixed into a fluid paste, poured into a flat Petri dish and left to polymerize for 24 h to obtain a 1.5 mm thick sheet. Rectangular sections (1.5×1.5×6 mm) are cut out from the sheet using a hand press and a suitable punch and die. The needles with square section thus obtained demonstrated their injectability in a porcine skin model. Release of the contained albumin was determined by incubation in 100 μl of buffered saline (pH7.4) at 37° C. and colorimetric determination using Comassie G-250 (Bradford assay) at 595 nm. After 24 h injectable needles have released 40% of the contained albumin.

Example 11

Injectable Needles that Incorporate Adjuvant Modifying Agents

Poly(D,L-lactide-co-glycolide) 50:50, 140 mg; camphorquinone, 3.5 mg, acrylic acid, 650 mg, diethyleneglycol diacrylate, 950 mg, (2-N,N-dimethylamino)ethyl methacrylate, 140 mg, are thoroughly mixed. Optionally 1 mg of a synthetic oligonucleotide containing CpG is added to the mixture as adjuvant agent.

Microparticles consisting of 90.5% trehalose, 2% polyvinylpyrrolidone, and 7.5% of hepatitis B surface antigen (HBsAg), as a model drug, and particle size between 1 to 10 μm are produced by spray-drying. The microparticles, 500 mg, are thoroughly dispersed into the mixture of polymers, monomers, and initiator, and the resulting paste is injected into 1 mm internal diameter transparent silicone tube as a mould. The mixture is made to polymerize by irradiation with blue-violet light for 10 minutes. The silicone tube with polymerized material is cut into 10 mm long sections to provide with the injectable needles.

Needles, with (A) and without CpG (B) were implanted in BalbC C3H mice, 9 mice per experimental group, and antibody titres in blood against HBsAg determined by ELISA after 28 days compared with mice vaccinated with Recombivax HB (Merck) (C) as shown in Table 3. All mice showed seroprotection with levels over 10 U/I. Incorporation of CpG to the injectable needles as an adjuvant modifying agent resulted increased antibody titres.

TABLE 3

| | Antibody Titre HBsAc (U/l) | SD (U/l) |
|---|---|---|
| A) Injectable Needle | 39.6 | 8.6 |
| B) Injectable Needle + CpG | 60.3 | 7.4 |
| C) Recombivax | 40.4 | 6.5 |

Example 12

Injectable Needles that Incorporate Cross-Linker Monomers to Modulate Stiffness and Biodegradability Polymerizable pastes are prepared by mixing the components listed in Table 4. The pastes are moulded into bars of 2×2×25 mm and photopolymerized irradiating with filtered halogen light (λ=440-480 nm, 1,400 mW/cm2) for 10 min. Polymerized bars are used for determination of the flexural strength according to ISO 4049 standard.

The pastes are moulded into disks of 13 mm diameter and 2 mm height. The discs are incubated in water at 37° C. After 24 h, the disks are removed, wiped and let dry at air to constant weight and the weight loss in percent of the initial weight is determined. The pastes are also fed to the chamber of a high-pressure microextruder device fitted with a 0.686 mm interior diameter nozzle. The paste is extruded and at the same time is polymerized by irradiation with filtered halogen light (λ=440-480 nm, 1,400 mW/cm2) for 10 min. The extruded mass is cut in needles of 3-4 mm in length that are loaded in a delivery device for injection into a silicone block used as skin model, and the penetrability is evaluated.

The results of Table 4 show that cross-linker reduces the weight-loss and release-rate, that is, the solubility or resorption of the material used to manufacture the injectable needles. On the other hand, the cross-linker increases the flexural strength of the materials and the penetrability of the needles.

TABLE 4

| Components of the polymerization reaction | Weigth Loss | Release Rate | Flexural strength | Penetra-bility |
|---|---|---|---|---|
| Acrylic acid 105 mg; (2-N,N-dimethylamino)ethyl acrylate 95 mg; Poly(N-vinylpyrrolidone) 65 mg; camforquinone 1.2 mg | 100% | n.d. | 12 ± 2 MPa | n.d. |
| Acrylic acid 105 mg; (2-N,N-dimethylamino)ethyl acrylate 95 mg; Poly(N-vinylpyrrolidone) 65 mg; tri(propylene glycol) diacrylate 1.7 mg; camforquinone 1.2 mg; | 48% | n.d. | 16 ± 2 MPa | n.d. |
| Acrylic acid 105 mg; (2-N,N-dimethylamino)ethyl acrylate 95 mg; Poly(N-vinylpyrrolidone) 65 mg; tri(propylene glycol) diacrylate 6 mg; camforquinone 1.2 mg | 28% | n.d. | 18 ± MPa | n.d. |
| Acrylic acid 105 mg; (2-N,N-dimethylamino)ethyl acrylate 95 mg; Poly(N-vinylpyrrolidone) 65 mg; Coomassie Blue R-250 35 mg; camforquinone 1.2 mg | n.d. | +++++ | n.d. | +++ |
| Acrylic acid 105 mg; (2-N,N-dimethylamino)ethyl acrylate 95 mg; Poly(N-vinylpyrrolidone) 65 mg; Coomassie Blue R-250 35 mg; tri(propylene glycol) diacrylate 1.7 mg; camforquinone 1.2 mg; | n.d. | ++++ | n.d. | ++++ |
| Acrylic acid 105 mg; (2-N,N-dimethylamino)ethyl acrylate 95 mg; Poly(N-vinylpyrrolidone) 65 mg; Coomassie Blue R-250 35 mg; tri(propylene glycol) diacrylate 6 mg; camforquinone 1.2 mg; | n.d. | +++ | n.d. | +++++ | n.d. non-determined

The invention claimed is:

1. An injectable needle, with a diameter ranging from 0.2 to 2 mm, comprising:
   a) 30% to 90% in mass of a solid polymeric matrix continuous phase having a flexural strength over 10 MPa and comprising (i) an addition polymer formed by the polymerization of addition monomers, wherein the addition polymer is selected from the group consisting of polycyanoacrylates, polyacrylates, polymethacrylates, polyvinyls, and any combination thereof, and (ii) a polymeric modifying agent selected from the group consisting of polylactides, polyglycolides, polylactide-co-glycolides or polyvinylpyrrolidones, and any combination thereof, wherein the polymeric matrix is at least partially biodegradable or resorbable, and
   b) a solid discontinuous water-soluble phase containing a drug preformulated as particles or granules having a diameter between about 0.02 and about 500 microns, the solid discontinuous water-soluble phase in direct contact with the solid polymeric matrix,
   wherein the injectable needle is formed within a mold by polymerization of the addition monomers in the presence of the polymeric modifying agent to form an interpenetrating polymeric network (IPN) that incorporates the solid discontinuous water-soluble phase.

2. The injectable needle of claim 1, wherein the polyacrylate is selected from: polyacrylic acid, polyacrylamide, poly-N-isopropylacrylamide, alkaline polyacrylate, alcaline-terreus polyacrylate, ammonium polyacrylate, or any of their combinations.

3. The injectable needle of claim 1, wherein the polymethacrylate is selected from: polymethacrylic acid, alkaline polymethacrylate, alkaline-terreous polymethacrylate, ammonium polymethacrylate, 2-hydroxypropyl polymethacrylate, (2-dimethylamino)ethylpolymethacrylate, 1-glycerol polymethacrylate, polymethacrylamide, or any of their combinations.

4. A method for the manufacture of the injectable needle of claim 1 which comprises:
   a.) mixing the addition monomers and the polymeric modifying agent with the solid discontinuous water-soluble phase containing the drug, preformulated as particles or granules having a diameter between about 0.02 and about 500 microns to form a paste, and
   b.) polymerizing the resulting paste within a mold to form an injectable needle having an interpenetrating polymeric network (IPN) that incorporates the solid discontinuous water-soluble phase containing the drug particles or granules having a diameter between about 0.02 and about 500 microns, wherein:
   (i) the injectable needle has a diameter ranging from 0.2 to 2 mm and comprises 30% to 90% in mass of a solid polymeric matrix continuous phase having a flexural strength over 10 MPa and comprising an addition polymer formed by the polymerization of the addition monomers, wherein the addition polymer is selected from the group consisting of polycyanoacrylates, polyacrylates, polymethacrylates, polyvinyls, and any combination thereof, and (ii) a polymeric modifying agent selected from the group consisting of polylactides, polyglycolides, polylactide-co-glycolides or polyvinylpyrrolidones, and any combination thereof, wherein the polymeric matrix is at least partially biodegradable or resorbable, and
   (ii) the solid discontinuous water-soluble phase is in direct contact with the solid polymeric matrix continuous phase.

5. The method of claim 4, wherein the polymerization reaction is a polyaddition reaction that is catalysed photochemically.

6. A method for percutaneous administration of a drug for the treatment, prevention or diagnosis of a human or animal disease which comprises:
   providing an animal or human in need of said drug and
   administering said drug to the animal or human by the injectable needle of claim 1.

* * * * *